United States Patent [19]

Warren

[11] Patent Number: 5,073,657
[45] Date of Patent: Dec. 17, 1991

[54] VAPOR PHASE MODIFIERS FOR OXIDATIVE COUPLING

[75] Inventor: Barbara K. Warren, Charleston, W. Va.

[73] Assignee: Union Carbide Chemicals and Plastics Company Inc., Danbury, Conn.

[21] Appl. No.: 409,361

[22] Filed: Sep. 19, 1989

[51] Int. Cl.$^5$ ................................................. C07C 2/00
[52] U.S. Cl. ................................... 585/500; 585/657; 585/658; 585/700; 585/943
[58] Field of Search ............... 585/500, 657, 658, 943, 585/700

[56] References Cited

U.S. PATENT DOCUMENTS

| | | | |
|---|---|---|---|
| 4,199,533 | 4/1980 | Benson | 585/500 |
| 4,450,310 | 5/1984 | Fox et al. | 585/700 |
| 4,465,893 | 8/1984 | Olah | 585/709 |
| 4,544,784 | 10/1985 | Sofranko et al. | |
| 4,634,800 | 1/1987 | Withers et al. | 585/658 |
| 4,654,459 | 3/1987 | Sofranko | 585/500 |
| 4,654,460 | 3/1987 | Kimble et al. | |
| 4,731,498 | 3/1988 | Devries et al. | 585/500 |
| 4,769,504 | 9/1988 | Noceti et al. | 585/657 |
| 4,795,842 | 1/1989 | Gaffney | 585/654 |

FOREIGN PATENT DOCUMENTS 52925  1/1986  Australia .

OTHER PUBLICATIONS

The Enhancement of the Oxidative Coupling of Methane on Oxide/SiO$_2$ Catalysts by Tetrachloromethane, Ahmed et al, Catalyst Lett. 2 (1989) 309–318.
Otsuka, et al., "Active and Selective Catalysts in Oxidative Coupling of Methane, Nickel Oxides with Salts of Alakli Metals", Inorg. Chim. Acta, vol. 118, L23–L24 (1986).
Otsuka, et al., "Synthesis of Ethylene by Partial Oxidation of Methane over the Oxides of Transition Elements with LiCl", Chem. Soc. Japan, Chem. Lett., 903–906 (1986).
Fujimoto, et al., "Selective Oxidative Coupling of Methane Over Supported Alkaline Earth Metal Halide Catalysts", Appl. Catal., vol. 50, 223–236 (1989).
Burch, et al., "Role of Chlorine in Improving Selectivity in the Oxidative Coupling of Methane to Ethylene", Appl. Catal., vol. 46, 69–87 (1989).

*Primary Examiner*—Patrick P. Garvin
*Assistant Examiner*—E. D. Irzinski
*Attorney, Agent, or Firm*—Jean B. Mauro

[57] ABSTRACT

Volatilized metal compounds retard vapor phase alkane conversion reactions in oxidative coupling processes that convert lower alkanes to higher hydrocarbons.

17 Claims, No Drawings

VAPOR PHASE MODIFIERS FOR OXIDATIVE COUPLING

This invention was made under United States of America Government support under Contract No. DE-AC22-87PC79817 awarded by the Department of Energy. The Government has certain rights in this invention.

RELATED APPLICATIONS

U.S. patent application Ser. No. 463,320, filed Jan. 10, 1990; U.S. patent application Ser. No. 542,699, filed June 25, 1990; U.S. patent application Ser. No. 543,393, filed June 26, 1990; all of which are commonly assigned.

The following are related, commonly assigned applications, filed on an even data herewith:

U.S. patent application Ser. No. 409,375; U.S. patent application Ser. No. 409,544; U.S. patent application Ser. No. 409,376; U.S. patent application Ser. No. 409,369; and U.S. patent application Ser. No. 409,359.

This invention relates to processes for the oxidative coupling of lower molecular weight alkane to higher molecular weight hydrocarbons.

BACKGROUND OF THE INVENTION

Processes for the conversion of lower molecular weight alkanes such as methane to higher molecular weight hydrocarbons which have greater value are sought. One of the proposals for the conversion of lower molecular weight alkanes is by oxidative coupling. For instance, G. E. Keller and M. M. Bhasin disclose in *Journal of Catalysis*, Volume 73, pages 9 to 19 (1982) that methane can be converted to, e.g., ethylene. The publication by Keller, et al., has preceded the advent of substantial patent and open literature disclosures by numerous researchers pertaining to processes for the oxidative coupling of lower alkanes and catalysts for such processes.

In order for an oxidative coupling process to be commercially attractive, the process should be capable of providing a good rate of conversion of the lower alkanes with high selectivity to the sought higher molecular weight hydrocarbons.

Two general types of oxidative coupling processes are the sequential, or pulsed, processes and the cofeed processes. The sequential processes are characterized by alternately cycling an oxygen-containing gas and an alkane-containing gas to contact a catalyst. These processes typically provide high selectivities to higher hydrocarbon but suffer from operational complexities in cycling the catalyst environment and in the tendency of the processes to produce less desirable, higher molecular weight products and to have carbonaceous deposits form on the catalyst, thereby necessitating regeneration. Thus, from an operational standpoint, cofeed processes, i.e., processes in which oxygen-containing material and alkane are simultaneously fed to the reaction zone containing the catalyst, are more desirable.

In order for cofeed processes to be commercially attractive, especially for the production of large volume commodity chemicals such as ethylene and ethane ($C_2$'s), the conversion of alkane should be high as well as the higher hydrocarbons as opposed to combustion products such as carbon dioxide and carbon monoxide.

Oxidative coupling occurs in the absence of catalysts, and this can occur in a homogeneous phase with oxygen and lower alkane being converted to carbon oxides (predominantly carbon monoxide) and higher hydrocarbons. The reaction proceeds at elevated temperatures, usually in excess of 600° C. In order to enhance conversions of the lower alkane and selectivities to the higher hydrocarbons, catalysts have been used. Heterogeneous reactions are believed to occur on the surface of the catalysts.

Numerous researchers have studied the mechanisms by which oxidative coupling occurs. See, for instance, Campbell, et al., "Gas-Phase Coupling of Methyl Radicals during the Catalytic Partial Oxidation of Methane", J. Am. Chem. Soc., Vol. 109, 7900 (1987); Hutchings, et al., "The Role of Gas Phase Reaction in the Selective Oxidation of Methane", J. Chem. Soc., Chem. Comm., 253 (1988); Otsuka, et al., "Synthesis of $C_2H_4$ by Partial Oxidation of $CH_4$ over Transition Metal Oxides with Alkali Chlorides", Studies in Surface Science & Catalysis: #36 Methane Conversion Symp., Auckland, New Zealand (1987); Yates, et al., "Blank Reactor Corrections in Studies of the Oxidative Dehydrogenation of Methane", J. Catal., Vol. 111 (1988); Driscoll, et al., "Gas-Phase Radical Formation during the Reactions of Methane, Ethane, Ethylene and Propylene over Selected Oxide Catalysts", J. Phys. Chem., Vol. 89, 4415 (1985); Driscoll, et al. "The Production of Gas Phase Methyl Radicals over Li/MgO", in Che, et al., eds., *Adsorption & Catalysis on Oxide Surfaces*, Elsevier Science Publishers B. V., Amsterdam (1985); Hatano, et al., "Alkali Metal Doped Transition Metal Oxides Active for Oxidative Coupling of Methane", Inorg. Chim. Acta, Vol. 146, 243 (1988); Minachev, et al., "Oxidative Coupling of Methane", Russian Chem. Reviews, Vol. 57, 221 (1988); Shigapov, et al., "Peculiarities in Oxidative Conversion of Methane to $C_2$ Compounds over $CaO-CaCl_2$ Catalysts", React. Kinet. Catal. Lett., Vol. 37, 397 (1988); Burch, et al., "Comparative Study of Catalysts for the Oxidative Coupling of Methane", Appl. Catal., Vol. 43, 105 (1988); Martin, et al., "Oxidative Conversion of Methane and $C_2$ Hydrocarbons on Oxides: Homogeneous versus Heterogeneous Processes," Appl. Catal., Vol. 47, 287 (1989); Lane, et al., "Methane Utilization by Oxidative Coupling,"J. Catal., Vol. 113, 114 (1988) and Asami, et al., "Vapor-Phase Oxidative Coupling of Methane under Pressure," Energy & Fuels, Vol. 2, 574 (1988).

A thread from the mechanisms postulated by these workers is that even in heterogeneous catalysts systems, homogeneous reactions occur in the vapor phase. Many propose that the catalyst serves to generate, e.g, methyl radicals which are then coupled in the vapor phase to produce ethane or ethylene ($C_2$'s). Yates, et al., for instance, show at 700° C., in an empty reactor 23 percent of the methane can be converted with a selectivity to $C_2$'s (ethylene and ethane) of 20.9 percent. Hence, vapor phase oxidation of alkane can be material to the performance of a catalytic process. Hatano, et al., supra, opine that the stability of the solid solution of alkali metals with transition metal oxides under steady state reaction conditions is essential for the alkali-doped oxide to be effective in the oxidative coupling of methane. Shigapov, supra, postulates that the chloride radicals associated with, e.g., calcium chloride, are responsible for increasing selectivity.

Among the numerous catalysts which have been proposed by researchers for oxidative coupling processes include catalysts containing alkali and/or alkaline earth metals. The alkali and alkaline earth metals have been suggested as being in the oxide, carbonate and halide forms. Other components such as rhenium, tungsten, copper, bismuth, lead, tin, iron, nickel, zinc, indium, vanadium, palladium, platinum, iridium, uranium, osmism, rhodium, zirconium, titanium, lanthanum, aluminum, chromium, cobalt, beryllium, germanium, antimony, gallium, manganese, yttrium, cerium, praseodymium (and other rare earth oxides), scandium, molybdenum, thallium, thorium, cadmium, boron, among other components, have also been suggested for use in oxidative coupling catalysts. See, for instance, U.S. Pat. Nos. 4,450,310; 4,443,646; 4,499,324; 4,443,645; 4,443,648; 4,172,810; 4,205,194; 4,239,658; 4,523,050; 4,442,647; 4,499,323; 4,443,644; 4,444,984; 4,659,668; 4,704,487, 4,777,313; 4,780,449; International Patent Publication WO 86/07351, European Patent applications nos. 189079 (1986); 206042 (1986); 206044 (1986), and 177327 (1985), Australian Patent No. 52925 (1986), Moriyama, et al., "Oxidative Dimerization of Methane Over Promoted MgO, Important Factors," Chem. Soc. Japan, Chem. Lett., 1165 (1986), and Emesh, et al., "Oxidative Coupling of Methane over the Oxides of Groups IIIA, IVA and VA Metals," J. Phys. Chem, Vol. 90, 4785 (1986).

In many instances, the literature and patents describing oxidative coupling processes and catalysts do not relate experiences with catalyst stability. However, due to the lifetime problems that have plagued oxidative coupling catalysts, skepticism appears to exist that oxidative coupling catalysts exhibit long useful lifetimes absent empirical demonstrations.

Several researchers have attributed deactivation in certain catalysts to the loss of volatile salts from the catalyst. Otsuka, et al., note in "Active and Selective Catalysts in Oxidative Coupling of Methane. Nickel Oxides with Salts of Alkali Metals," Inorg. Chim. Acta, Vol. 118, L23 (1986), that the loss of catalyst performance could be due to the alkali salts investigated not being stable under oxidative coupling reaction conditions. They suggest that the salts may decompose, evaporate, react with methane and oxygen, or produce mixed oxides with NiO. Otsuka, et al., in "Synthesis of Ethylene by Partial Oxidation of Methane over the Oxides of Transition Elements with LiCl." Chem. Soc. Japan, Chem. Lett., 903 (1986), states that lithium chloride was found deposited at the outlet of the reactor. Fujimoto, et al., in "Selective Oxidative Coupling of Methane Over Supported Alkaline Earth Metal Halide Catalysts,"Appl. Catal., Vol. 50, 223 (1989), state that ". . . the decrease in catalytic activity for $C_2$ formation over the $MgCl_2/CaO$ catalyst can be attributed to the loss of halide ion." ". . . by replenishing the trace amount of chloride from the vapor phase with chloroform no change in selectivity was observed . . ." (p.227, 228).

Several researchers have proposed the use of alkali or alkaline earth metals in the form of halides (e.g., chloride, bromide or iodide) in oxidative coupling catalysts. The addition of hydrogen halide, halogen and/or organic halide has also been proposed. Australian Patent No. 52925 discloses the use of supported calcium chloride, barium bromide, potassium iodide, lithium chloride, cesium chloride, among others, for catalysts to oxidatively couple methane to ethane and ethylene. The patentees disclose feeding hydrogen halide to the reaction zone. European Patent Application 210 383 (1986) discloses the addition of gas phase material containing halogen component such as chlorine, methyl chloride and methyl dichloride. Enhanced selectivities are reported when the halogen component is present. The catalysts include those containing one or more of alkali and alkaline earth metal, alkali metal with lanthanide oxide, zinc oxide, titanium oxide or zirconium oxide, and others. The applicants postulate that the halide is important to increase conversion, especially to unsaturated materials. U.S. Pat. No. 4,654,460 discloses the addition of a halogen-containing material either in the catalyst or via a feed gas in an oxidative coupling process. The catalyst contains one or more alkali metal and alkaline earth metal components. Although no working examples are provided, conversions of methane are said to be increased with halides and selectivities to higher hydrocarbons, particularly ethylene, occur. See also, Burch, et al., "Role of Chlorine in Improving Selectivity in the Oxidative Coupling of Methane to Ethylene," Appl. Catal., Vol. 46, 69 (1989), who propose mechanistic possibilities for the effect of halide in oxidation coupling of methane.

Burch, et al., in their 1989 article, supra, queried whether the instability of metal halide-containing catalysts could be remedied by the addition of gaseous chlorinated compounds such as dichloromethane. They also indicate that the influence of the chloride addition is relatively short-lived with the catalysts tested and therefore continuous addition of the chloride is suggested. From a mechanistic standpoint, the authors opine that chlorides inhibit total oxidation and promote dehydrogenation of ethane.

U.S. Pat. No. 4,544,784 discloses the activation of certain catalysts for oxidative coupling of methane. The patentees state that methane conversion can be improved by at least periodic introduction of a halogen compound and that the presence of at least one alkali metal prolongs the effect provided by the addition of the halogen compound. The halogen compounds proposed are hydrogen halides, ammonium halides, aromatic halides and halogen gas. (Column 6, line 45, et seq.).

Other reports of halide addition to processes for the oxidative coupling of methane include European Patent Application Publications Nos. 206,043, 216,948 and 198,251.

SUMMARY OF THE INVENTION

By this invention processes are provided for the oxidative coupling of lower alkane to produce heavier hydrocarbons in the presence of a catalytically-effective amount of heterogeneous oxidative coupling catalyst wherein vapor phase alkane conversion reactions are attenuated. In accordance with this invention, enhanced selectivity to higher hydrocarbons is obtained by feeding intermittently or continuously to the reaction zone an amount of at least one volatilized metal compound in an amount sufficient to inhibit vapor phase alkane conversion reactions. Thus, the alkane conversion reactions involving the heterogeneous catalyst are believed constitute a greater portion of the total alkane conversion reactions in the reaction zone and the selectivity benefits provided by the heterogeneous catalytic reactions can be better realized.

In one aspect of this invention, the volatilized metal compound comprises a metal which is at least as basic or electrophilic as lithium, and preferably, the metal is more basic or electrophilic than lithium. In another aspect of the invention, the volatilized metal compound comprises at least one alkali metal or alkaline earth metal compound.

In a preferred aspect of this invention, halogen-containing vapor phase additive is also fed intermittently or continuously to the reaction zone in an amount sufficient to enhance at least one of conversion of alkane and selectivity to higher hydrocarbon.

In the processes of this invention, lower alkane, e.g., 1 to about 3 carbon atoms is converted to heavier hydrocarbons by contacting in a reaction zone the alkane in the presence of reaction oxygen-containing material under oxidative coupling conditions with a catalytically-effective amount of heterogeneous oxidative coupling catalyst and feeding to the reaction zone intermittently or continuously an amount of at least one volatilized metal compound in an amount sufficient to inhibit vapor phase alkane conversion reactions. Advantageously, the amount of volatilized metal compound is sufficient to reduce the rate of the vapor phase alkane conversion reactions by at least about 50 percent as determined at 750° C. in a void reactor at 176 kPa absolute (11 pounds per square inch gauge) pressure.

Preferably, the volatilized component comprises alkali metal compounds, especially cesium compounds. The volatilized metal compounds are capable of exhibiting a vapor pressure under the oxidative coupling conditions and include oxides, hydroxides or salts, e.g., carbonates, phosphates, sulfates, halides (such as chlorides, bromides and iodides), oxyhalides ($OX^-$), halates ($XO^-_3$), halites ($XO^-_2$) and perhalates ($XO^-_4$) wherein X is one or more of chlorine, bromine and iodine. The amount of volatilized component is usually at least about 0.001 picogram per cubic meter (standard temperature and pressure) of alkane fed to the reaction zone.

The halogen-containing vapor phase additive is preferably a chlorine, iodine or bromine component and is in an amount sufficient to enhance the selectivity to higher hydrocarbons of the catalyst.

DETAILED DESCRIPTION OF THE INVENTION

In accordance with this invention, lower alkane is converted to higher hydrocarbons. The lower alkane preferably comprises at least one of methane, ethane and propane, and because of its abundance and the desire to convert it to higher hydrocarbons, methane is the most preferred component in the feed. The products of the conversion are higher hydrocarbons, especially alkanes and alkenes. Often, the desired conversion products are alkenes of two to four carbon atoms, especially ethylene and propylene. Because of its widespread use in commodity chemicals, product mixtures exhibiting a high selectivity to ethylene are typically preferred. The reaction is conducted in the presence of a reactive oxygen-containing material (oxidizing material) which for the purposes herein means atomic or molecular oxygen or a compound or chemical complex that contains an oxygen atom available for the oxidative coupling The hydrocarbon conversion process is by a cofeed, or simultaneous process, in which both the oxidizing material and the alkane-containing feed are provided at the same time to the reaction zone. In a cofeed mode, the oxidizing material and alkane may be introduced by one or more separate streams or, most commonly, in a premixed stream. Generally, the mole ratio of alkane to active oxygen atom of the oxidizing material (an active oxygen atom is an oxygen atom that is available for oxidation) is at least about 1:2, say, about 1:2 to 50:1, preferably 1:1 to 20:1. The alkane typically comprises at least about 2 volume percent, e.g., up to about 95, say, 5 to 90 volume percent of the total gases fed to the reaction zone. Frequently, the feed streams are diluted with essentially inert gases such as helium, nitrogen, argon, steam, and carbon dioxide. When diluted, the diluent usually provides between about 5 to 95 volume percent of the feed streams.

The oxidizing material may be any suitable oxygen-bearing material which, under the conditions in the reaction zone, yields an active oxygen atom for the oxidative coupling. While not wishing to be limited to theory, the oxygen atom may be provided as reactive in a gaseous zone and/or may be provided on a catalyst surface as, for instance, reacted, absorbed or adsorbed form. Convenient oxidizing materials are normally gaseous such as molecular oxygen, (e.g., as oxygen, enriched air or air), ozone and gases which yield oxygen such as $N_2O$. Materials that are liquid or solid at ambient conditions may also be used provided that they can be facilely introduced into the reaction zone.

The reaction proceeds at elevated temperatures. Generally, a minimum temperature must be achieved before significant high hydrocarbon production occurs. If the temperature is too high, an undue amount of the hydrocarbon is consumed in oxidation or degradation reactions. Often, the temperature is in the range of about 500° to 1000° C., e.g., about 600° to 800° C. The reactants are usually preheated prior to their introduction into the reaction zone; for instance, to within about 200° C., preferably about 100° C. of the temperature in the reaction zone.

The pressure in the reaction zone may vary widely from less than atmospheric to 100 atmospheres absolute or more. The pressure is often in the range of about 1 to 100, say, 1 to 50, atmospheres absolute.

In general, the reactions proceed rapidly and, hence, the reactants may reside in the reaction zone under reaction conditions for a relatively short period of time, e.g., less than about 20 seconds, often less than about 10 seconds. Frequently, the residence time is about 0.001 to 5, say, 0.1 to 3, seconds. The gas hourly space velocity based on the total gases fed to the reaction zone to the volume of the reaction zone is often about 50 to 50,000, preferably, 500 to 15000, reciprocal hours. Frequently, the volume of the reaction zone is calculated as the volume of the vessel filled with catalyst.

The reaction may be conducted in any suitable reactor capable of providing the reaction temperatures. The reaction may be conducted in a single or in a series of sequential and/or parallel reactors. The catalyst bed may be of any suitable type, including, but not limited to, fixed, fluid, riser, falling, ebulating, and moving bed.

A wide variety of oxidative coupling catalysts can be used in the processes of this invention. Oxidative coupling catalysts include those containing one or more metal oxides, hydroxides, peroxides, superoxides and/or salts of metals of Group IA (e.g., lithium, sodium, potassium, rubidium and cesium), Group IIA (e.g., beryllium, magnesium, calcium, barium, and strontium), Group IIIA (e.g, yttrium, lanthanum, lanthanide series elements such as praseodymium, samarium and gadolinium), Group IVA (e.g, titanium and zirconium), Group VIIA (e.g., manganese), Group VIIIA (e.g., nickel, iron and cobalt), Group IB (e.g., copper), Group IIB (e.g., zinc), Group IIIB (e.g., aluminum and gallium), Group IVB (e.g., germanium, tin and lead), and Group VB (e.g., antimony and bismuth). These metal compounds may be used in combination with others within the above listed group or with one or more other adjuvants containing, e.g., chromium, molybdenum, tungsten, rhenium, ruthenium, rhodium, osmium, iridium, palladium, platinum and silver. The compounds may be oxides, peroxides, superoxides, hydroxides or salts or combinations thereof. Salts include carbonates, phosphates, sulfates, halides ($X^-$), oxyghalides ($OX^-$) halites ($XO^-_2$), halates ($XO^-_3$) and perhalates ($XO^-_4$) wherein X is one or more of chlorine, bromine and iodine. The oxides may be mixed oxides and may be amorphous and/or crystalline, e.g., alpha alumina, molecular sieves, spinel, perovskites such as $ABO_3$ perovskites wherein A is alkaline earth metal and B is titanium, zirconium or cesium, and $A_2Ln_2C_3O_{10}$ perovskites wherein A is alkali metal, Ln is Group IIIA (including lanthanide series) metals, and C is titanium.

The catalysts may be supported or unsupported. When supported, the support may have catalytic activity or may be essentially inert, i.e., be catalytically acceptable.

The support material may comprise refractory oxides, e.g., alumina, zirconia, titania, silica, spinels, perovskites (e.g., $ABO_3$ wherein A is a Group IIA metal and B is a Group IVA metal), aluminosilicates, alkaline earth oxides (e.g., magnesium oxide, calcium oxide, barium oxide and strontium oxide); alkaline earth carbonates (e.g., barium carbonate and strontium carbonate), and the like. Advantageously, the support material has a surface area of at least about 0.1, preferably, at least about 0.2, say, 0.2 to 60 or 100 or more, square meters per gram. (Determined by the nitrogen B.E.T. Method, J. Am. Chem. Soc., Vol. 60, 309 (1938)).

As can be appreciated, it is possible that a portion of the volatilized component may deposit (at least temporarily) on the catalyst. Hence, often the volatilized component is selected on the basis of its performance as a component of a heterogeneous catalyst.

The components of the catalyst may be fabricated into a convenient catalyst configuration, e.g., through the use of binders. However, the catalyst is preferably supported on a support which is capable of withstanding the oxidative coupling conditions. The supported catalyst may be prepared by any convenient technique. Techniques which have been proposed include coating the catalyst support with a slurry or paste of the ingredients or impregnating the support using a solution or suspension or complex of the ingredients (the impregnation may be simultaneous for all components or sequential). The impregnation may be an incipient wetness technique or by immersion in the mother liquor or by evaporation of solvent from a solution or suspension containing the support. The catalysts may be dried and, optionally, calcined.

Barium and/or strontium compounds are preferred catalyst components. Often, these compounds are present in amounts of 0.1 to 20 or more weight percent based on the weight of the catalyst. These compounds are barium oxide, strontium oxide, barium peroxide, strontium peroxide, barium superoxide, strontium superoxide, barium hydroxide, strontium hydroxide, barium carbonate, strontium carbonate, barium halide ($BaX_2$), strontium halide, barium oxyhalide ($Ba(OX)_2$), strontium oxyhalide, barium halite ($Ba(XO_2)$, strontium halite, barium halate ($Ba(XO_3)_2$), strontium halate, barium perhalate ($Ba(XO_4)_2$, strontium perhalte, wherein X is one or more of chlorine, bromine and iodine, and mixtures thereof. The preferred barium compounds are barium oxide, barium dihalide, barium carbonate, and barium hydroxide, and the preferred strontium compounds are strontium oxide, strontium dihalide, strontium carbonate and strontium hydroxide.

Illustrative oxidative coupling catalysts are set forth in Table I.

TABLE I

| CATALYST | COMPONENTS | WEIGHT PERCENT |
|---|---|---|
| A | $Li_2CO_3/MgO$ | 0.01–50/50–99.99 |
| B | $NiCl/Al_2O_3$ | 0.01–30/70–99.99 |
| C | $NaCl/Al_2O_3$ | 0.01–30/70–99.99 |
| D | $KCl/Al_2O_3$ | 0.01–30/70–99.99 |
| E | $CsCl/Al_2O_3$ | 0.01–30/70–99.99 |
| F | $BaCl_2/Al_2O_3$ | 0.01–30/70–99.99 |
| G | $KCl/Ag/Al_2O_3$ | 0.01–10/0.01–30/60–99.98 |
| H | $BaCl_2/Ag/Al_2O_3$ | 0.01–10/0.01–30/60–99.98 |
| I | $Li_2B_4O_7/Al_2O_3$ | 0.01–30/70–99.99 |
| J | $MnCl_2/Al_2O_3$ | 0.01–30/70–99.99 |
| K | $BaO/Al_2O_3$ | 0.01–30/70–99.99 |
| L | $BaCl_2/La_2O_3/Ag/Al_2O_3$ | 0.01–10/0.01–10/0.01–30/50–99.97 |
| M | $SrCO_3/TiO_2$ | 0.01–50/50–99.99 |
| N | $BaCO_3/TiO_2$ | 0.01–50/50–99.99 |
| O | $La_2O_3$ | |
| P | $BaCO_3$ | |
| Q | $BaCl_2/BaCO_3$ | 0.01–50/50–99.99 |
| R | $K_2La_2Ti_3O_{10}$ | |
| S | $Na_2La_2Ti_3O_{10}$ | |
| T | $SrCO_3/Al_2O_3$ | 0.01–50/50–99.99 |
| U | $BaCO_3/Al_2O_3$ | 0.01–50/50–99.99 |
| V | $CoO/BaCO_3/Al_2O_3$ | 0.001–2/0.01–50/50–99.999 |
| W | $SrCO_3$ | |

See, for instance, U.S. patent applications 409,359, 409,375, 409,376, 409,369 and 409,544, filed on even date herewith, hereby incorporated by reference.

The catalyst size and configuration may vary depending upon the reactor type. For fluid, ebulating and riser reactors, the catalyst is typically between about 30 and 300 microns in major dimension. In fixed bed reactors, the catalyst may be in any suitable configuration including spheres, pellets, cylinders, monoliths, etc., and the size and shape may be influenced by pressure drop considerations for the gases passing through the bed. Often, the catalyst is at least about 0.2 centimeter, say, about 0.5 to 2 centimeters, in major dimension. Monolithic catalysts, which may comprise a support having the catalytically active component thereon or which may be homogeneous, can be sized to fit the reactor volume.

With many catalyst systems, a halogen-containing vapor phase component may advantageously be provided to the reaction zone during the process. When halogen-containing component is provided to the reaction zone during the process, it may be added intermittently or continuously. The halogen-containing component may be provided as a solid, liquid or vapor under the conditions of the catalyst when added. The halogen-containing component may be halogen, e.g., chlorine, bromium or iodine, or a halogen-containing compound. The halogen-containing compounds may be inorganic or organic such as hydrogen halide, alkali metal halide, alkaline earth metal halide, silicon tetrahalide, carbon tetrahalide, phosphorus trihalide, methylene halide, methyl dihalide, methyl trihalide, ethyl halide, ethyl dihalide, ethyl trihalide, ethyl tetrahalide, vinyl halide, sulfonyl chloride, phosphonyl chloride, etc. Often, the organic halides have from 1 to 3 halogen atoms and 1 to 3 carbon atoms. Preferably, the halogen-containing component is provided as hydrogen halide, halogen or organic halide. The amount of halogen-containing component which can be added to the process, in general, depends upon the manner of addition. With a continuous vapor phase addition, too much halogen component can unduly retard the catalytic reaction and may even poison the catalyst. Conversely, with too little halogen component being added, the selectivity to higher hydrocarbons and/or conversion activity will be adversely affected. Also, the type of halogen being added will influence the performance of the reaction system. Within these guidelines, the amount of continuous vapor phase addition of the halogen component is often within the range of 0.1 to 5000, say, 1 to 1000, parts per million by volume based on the volume of feed to the reaction zone.

The volatilized metal component is introduced intermittently or continuously into the reaction zone in an amount sufficient to reduce the rate of vapor phase alkane conversion reaction. The specific reactions which are being retarded and where they may occur is not known; however, it is believed that reactions occurring in regions other than the catalyst surface that generate carbon oxides and that produce hydrocarbon radicals, are rate reduced. In the absence of catalyst, alkane conversion to both higher hydrocarbons and carbon oxides is lowered when the volatilized metal component is introduced. Hence, regardless of the nature and site(s) of the reaction(s), they are referred to herein as vapor phase alkane conversion reactions. It has not been ascertained whether the volatilized metal component has an effect on catalyst performance, and if so, what catalyst systems and to what extent the effect occurs; however, it is believed that for some catalyst systems, reactions on the catalyst that generate carbon oxides may also be retarded.

Often, the amount of volatilized metal component introduced is sufficient to reduce the rate of vapor phase alkane conversion by at least 50, preferably at least 70, percent. The reduction in vapor phase alkane conversion can be ascertained by operating the reaction zone with an essential absence of heterogeneous catalyst (preferably a void exists in the reaction zone) under the intended process conditions with the amount of volatilized metal component intended to be used and with no volatilized metal component, keeping feed flow rates the same. The alkane conversions under these two conditions are used to determine the percent reduction in the rate of vapor phase alkane conversion.

In practice, the amount of volatilized metal component to be added can be ascertained by monitoring the selectivity to higher hydrocarbons and adjusting the amount introduced. The amount of volatilized metal component introduced can vary widely and will depend, to some extent, on the nature of the volatilized metal component. Often, the amount of volatilized metal component introduced is at least about 0.001 picogram, say, about 0.005 picogram to 10,000 or more milligrams per cubic meter of alkane in the feed (determined at standard temperature and pressure ("STP")).

It is not essential, and indeed in most instances it is not the case, that the volatilized metal component has a boiling point below the reaction temperature. Most convenient volatilized metal components have boiling points much higher than the reaction temperature under reaction conditions. However, the volatilized metal component should have a vapor pressure under the reaction conditions sufficient to provide the sought amount of volatilized metal component to achieve the sought reduction in vapor phase alkane conversion. Accordingly, the volatilized metal components are preferably molten or near to becoming molten (e.g, within 100° C.) at the reaction temperature. The melting points of some volatilized metal components are set forth in Table II.

TABLE II

| VOLATILIZED COMPONENT | APPROXIMATE MELTING POINT (°C.) |
|---|---|
| Barium chloride | 963 |
| Strontium chloride | 875 |
| Barium bromide | 847 |
| Sodium chloride | 801 |
| Calcium chloride | 782 |
| Potassium chloride | 770 |
| Sodium bromide | 758 |
| Barium iodide | 740 |
| Potassium bromide | 730 |
| Rubidium chloride | 718 |
| Potassium iodide | 686 |
| Sodium iodide | 653 |
| Cesium chloride | 645 |
| Strontium bromide | 643 |
| Cesium iodide | 612 |
| Lithium chloride | 605 |
| Barium hydroxide | 408 |
| Potassium hydroxide | 405 |
| Sodium hydroxide | 318 |
| Cesium hydroxide | 272 |

The preferred volatilized metal components are salts of Group IA and Group IIA metals. Salts such as nitrates, chromates, etc., may have explosive characteristics at the reaction temperatures. Thus, these salts and other which may adversely decompose or oxidize are generally avoided. The volatilized metal component, however, may be added in the form of an oxide, hydroxide, peroxide, superoxide or salt and be converted to another compound under the reaction conditions. In general, the preferred salts are halides, especially chlorides, bromides and iodides.

The introduction of the volatilized metal component into the reaction zone may be by any convenient means. Advantageously, the volatilized metal component is relatively uniformly distributed as it passes through the reaction zone. The introduction may be, for instance, by adding a stream of volatilized metal component in the vapor form to the reaction zone or to the feed stream. Since most volatilized metal components are not gasses under the reaction conditions, the volatilized metal components must enter the vapor phase through sublimation or the effects of partial pressure over the metal component in the liquid state. Hence, it is often desirable to pass, at an elevated temperature (e.g. 400° to 1000° C., say 500° to 850° C.), all or a portion of the feed gas over the metal component to volatilize a desired amount of the metal component. Since oxidation reactions can occur at these elevated temperatures, frequently the volatilized metal component is contacted with either an alkane-containing stream having an essential absence of oxygen or a diluent gas or an oxygen-containing stream having an essential absence of alkane. The stream can be admixed with the remaining portion of the feed gases (for a continuous process).

In the event that the volatilized metal component solidifies, coalesces or is absorbed or absorbed in the reaction zone, a build-up of the volatilized metal component may occur. In many instances, the build-up is not unduly deleterious; however, if it adversely affects the performance of the reaction, temporary cessation of the introduction of the volatilized metal component may be indicated.

In another aspect of the invention, the volatilized metal component is removed from the reaction product downstream of the reaction zone. The removal may be by one or more unit operations such as condensation, coalescing and solidification, filtration of solids, absorption (such as in water for soluble volatilized metal components) and adsorption. Advantageously, at least a portion of the removed volatilized metal component is recycled.

The following examples are provided by way of illustration of the invention and are not in limitation thereof. All parts and percentages of solids are by weight and of liquids and gases are by volume unless otherwise noted or clear from the context.

The catalysts are evaluated using a reactor system containing a 77 centimeters long quartz tube containing a reaction zone. The reactor is operated vertically and heated by two ovens stacked vertically, so as to provide two distinct temperatures for the top and bottom portions of the reactor. The quartz tube (1.5 centimeters inside diameter and 1.7 centimeters outside diameter) is formed with a quartz pocket in an upper portion of the tube (4.5 centimeters from the top). The pocket is welded to the inside surface of the tube, has an outside diameter of 1.4 centimeters and an inside diameter of 1.2 centimeters, and extends downward from the weld so as to form an annular passageway between the inside of the tube and the outside of the pocket. A gas inlet (for methane) is provided proximate to the point where the pocket and tube are joined so that the methane passes into the annular passageway. The pocket extends downwardly for about 34.5 centimeters and the bottom is open. An oxygen and nitrogen mixture passes from the top of the tube into the pocket and exits from the opening at the bottom of the pocket where it is admixed with the methane exiting from the annular passageway.

A cup, having a 0.9 centimeter inside diameter, a 1.1 centimeters outside diameter and a length of 5.5 centimeters is axially positioned in the pocket (fused with quartz spacers) about 16.5 centimeters from the top of the tube. The upper end is open while the lower end of the cup is sealed. The cup holds the metal compounds which are to be volatilized during operation.

Two Research Inc. IR ovens, with approximately 1000° C. maximum operating temperature, are used for heating the quartz tube. Each oven connects to its own phase angle power control (series 663), 240 volts, 25 amps, with line and load voltage regulation capability which is further connected to an Athena controller (Model 4000-S-E, 25 amp).

The two ovens are equipped with chromel-alumel (type K) thermocouples which are used to measure the temperature of the furnaces. Temperature measurements can be inaccurate with direct IR-heating of the thermocouple, so the top part of the quartz tube is surrounded by a 3.6 centimeters outside diameter, 3.4 centimeters inside diameter, 27 centimeters long stainless steel tube, and the bottom part of the quartz tube is surrounded by a similar stainless steel tube but 37 centimeters long. The top oven (T. O.) center is 43.5 centimeters above the bottom of the reactor and the bottom oven (B. O.) center is 13.4 centimeters above the bottom of the reactor. The reactor is insulated at the reactor inlet and outlet ends and between the ovens and the two stainless steel tubes, with fibrafax insulating material.

In the general operating procedure, in experiments where catalyst is used, the catalyst bed is formed in the reactor by placing quartz wool in the bottom portion of the inverted quartz reactor, followed by catalyst then another plug of quartz wool, followed by about 58 grams of quartz chips (14 to 30 mesh, U. S. Sieve Series) held in place by quartz wool, so that the catalyst bed is centered in the bottom IR oven when the reactor is correctly positioned. When no catalyst is used in the bottom portion of the reactor, 21 grams of quartz chips (14 to 30 mesh, U. S. Sieve Series) are placed in the bottom cool region of the lower over, held in place by quartz wool, unless otherwise stated (unless the bottom was packed with alumina). Metal compounds are placed in the cup in the quartz reactor. The tubular quartz reactor, surrounded by the two portions as described above, is positioned in the furnaces. A 160 sccm flow rate is used for all experiments unless otherwise specified. When ethyl chloride is fed to the reactor, it is added with the methane. Nitrogen is turned on to the reactor. Reaction gases are introduced to the reactor. In most cases, the bottom oven is heated to the desired temperature, then the top oven is heated. After experiments, the reactant flow is terminated and the reactor is flushed with nitrogen while cooling. The reactor pressure is about 176 kPa absolute (11 pounds per square inch gauge) and nitrogen is the diluent gas. The feed for all experiments contains $CH_4/O_2/N_2$ in a mole ratio of about 2/1/7.

The results are provided in Table III. Conversions and selectivities are in mole percent. In Table III, the following defined terms are used:

| Temp | Temperature of the relevant ovens (°C.). |
|---|---|
| Time | Time since reactant flow is started (minutes). |
| $CH_4$ Conv. | Mole % of methane reacted. |
| Total $C_2$ Sel. | Selectivity to ethane + ethylene expressed as a percent, based on methane reacted. |

The product gas composition is in volume percent. The $CH_4$ Preheat Temp, °C., is the temperature of the top oven and the reactor Temp, °C., is the temperature of the bottom oven. Dashes indicate when amounts are too small to be accurately measured.

TABLE III

| Example Sel. % | Reactor Temp, °C. | $CH_4$ Preheat Temp, °C. | Time (min) | $CH_4$ Conv. % | % $CO_2$ | % CO | % $C_2H_6$ | % $C_2H_4$ | Total $C_2$ Sel, % |
|---|---|---|---|---|---|---|---|---|---|
| 1[a] | 750 | 232 | 115 | 27.27 | 0.377 | 5.557 | 0.213 | 0.467 | 18.47 |
| (comparative) | 700 | 218 | 195 | 20.99 | 0.247 | 4.467 | 0.207 | 0.313 | 18.03 |
| | 650 | 203 | 1420 | 7.20 | 0.014 | 0.731 | 0.093 | 0.035 | 25.66 |
| | 650 | 300 | 1560 | 8.63 | 0.028 | 1.214 | 0.113 | 0.058 | 21.62 |
| | 650 | 500 | 1675 | 8.50 | 0.028 | 1.244 | 0.117 | 0.060 | 21.65 |
| | 650 | 650 | 1980 | 6.63 | 0.020 | 0.949 | 0.102 | 0.004 | 23.05 |
| 2[b] | 650 | 225 | 105 | 5.23 | 0.021 | 0.823 | 0.101 | 0.042 | 25.28 |
| (comparative) | 650 | 300 | 160 | 3.52 | 0.009 | 0.365 | 0.069 | 0.017 | 31.61 |

TABLE III-continued

| Example | Reactor Temp, °C. | CH₄ Preheat Temp, °C. | Time (min) | CH₄ Conv. % | Product Gas Composition | | | | Total C₂ Sel. % |
|---|---|---|---|---|---|---|---|---|---|
| Sel. % | | | | | % $CO_2$ | % CO | % $C_2H_6$ | % $C_2H_4$ | |
| | 650 | 400 | 190 | 1.23 | 0.004 | 0.143 | 0.047 | 0.008 | 43.01 |
| | 700 | 400 | 215 | 5.36 | 0.031 | 0.758 | 0.117 | 0.058 | 30.55 |
| | 700 | 500 | 250 | 2.97 | 0.013 | 0.253 | 0.068 | 0.020 | 39.82 |
| | 700 | 600 | 275 | 3.27 | 0.023 | 0.388 | 0.075 | 0.026 | 32.98 |
| | 700 | 650 | 310 | 2.84 | 0.020 | 0.308 | 0.063 | 0.019 | 33.23 |
| | 650 | 225 | 1350 | 0.57 | 0.003 | 0.036 | 0.032 | 0.004 | 65.14 |
| 3[c] | 650 | 149 | 125 | 6.23 | 0.027 | 0.525 | 0.083 | 0.026 | 28.33 |
| (comparative) | 650 | 250 | 155 | 6.79 | 0.050 | 1.271 | 0.123 | 0.063 | 21.99 |
| | 650 | 300 | 215 | 10.43 | 0.053 | 1.349 | 0.125 | 0.067 | 21.52 |
| | 650 | 350 | 245 | 7.04 | 0.050 | 1.293 | 0.125 | 0.065 | 21.98 |
| | 650 | 400 | 295 | 9.36 | 0.049 | 1.222 | 0.117 | 0.061 | 21.87 |
| | 650 | 450 | 345 | 7.07 | 0.032 | 0.707 | 0.095 | 0.036 | 26.10 |
| | 650 | 500 | 375 | 4.17 | 0.029 | 0.257 | 0.050 | 0.011 | 29.85 |
| 4[d] | 650 | 196 | 95 | 5.34 | 0.023 | 0.771 | 0.096 | 0.039 | 25.35 |
| (Comparative) | 650 | 300 | 125 | 3.72 | 0.014 | 0.513 | 0.083 | 0.026 | 27.50 |
| | 650 | 400 | 160 | 5.57 | 0.031 | 1.069 | 0.112 | 0.054 | 23.08 |
| | 650 | 500 | 205 | 6.36 | 0.026 | 0.998 | 0.112 | 0.051 | 24.10 |
| | 650 | 600 | 245 | 0.77 | 0.005 | 0.043 | 0.032 | 0.005 | 60.45 |
| | 650 | 650 | 305 | — | 0.004 | 0.000 | 0.009 | 0.000 | 83.21 |
| | 700 | 650 | 365 | — | 0.016 | 0.085 | 0.037 | 0.008 | 47.17 |
| | 750 | 650 | 390 | 4.06 | 0.042 | 0.659 | 0.097 | 0.061 | 31.04 |
| | 750 | 700 | 420 | 3.48 | 0.035 | 0.550 | 0.089 | 0.051 | 32.02 |
| | 750 | 226 | 1400 | 15.49 | 0.134 | 2.463 | 0.188 | 0.266 | 25.58 |
| 5[e] | 650 | 165 | 85 | 3.14 | 0.008 | 0.359 | 0.059 | 0.014 | 28.58 |
| (Comparative) | 650 | 550 | 125 | 1.43 | 0.002 | 0.030 | 0.025 | 0.003 | 64.25 |
| | 650 | 600 | 155 | 0.64 | 0.003 | 0.069 | 0.031 | 0.005 | 50.06 |
| | 650 | 650 | 185 | — | 0.001 | 0.0027 | 0.022 | 0.003 | 64.60 |
| | 750 | 750 | 220 | 12.46 | 0.104 | 2.704 | 0.162 | 0.247 | 22.17 |
| | 850 | 850 | 300 | 30.36 | 4.481 | 2.634 | 0.020 | 0.120 | 3.75 |
| | 800 | 800 | 345 | 29.09 | 4.351 | 2.349 | 0.029 | 0.101 | 3.72 |
| | 750 | 183 | 1400 | 25.88 | 4.296 | 1.604 | 0.041 | 0.067 | 3.52 |
| 6[f] | 650 | 183 | 65 | 0.25 | 0.063 | 0.024 | 0.003 | 0.000 | 7.28 |
| (Comparative) | 650 | 650 | 100 | 0.48 | 0.084 | 0.007 | 0.005 | 0.000 | 9.24 |
| | 700 | 650 | 130 | 1.65 | 0.129 | 0.170 | 0.021 | 0.004 | 14.46 |
| | 700 | 700 | 160 | 1.85 | 0.110 | 0.187 | 0.021 | 0.004 | 14.28 |
| | 700 | 750 | 190 | 2.30 | 0.097 | 0.172 | 0.023 | 0.005 | 16.98 |
| | 750 | 750 | 3985 | 3.07 | 0.094 | 0.520 | 0.061 | 0.024 | 21.38 |
| | 750 | 195 | 4190 | 3.50 | 0.091 | 0.489 | 0.048 | 0.016 | 17.84 |
| 7[g] | 650 | 152 | 60 | 5.85 | 0.094 | 0.524 | 0.088 | 0.031 | 27.75 |
| (Comparative) | 650 | 200 | 90 | 5.79 | 0.117 | 0.798 | 0.105 | 0.045 | 24.49 |
| | 650 | 300 | 120 | 4.01 | 0.085 | 0.578 | 0.094 | 0.033 | 27.74 |
| | 650 | 400 | 160 | 6.50 | 0.114 | 0.964 | 0.113 | 0.053 | 23.58 |
| | 650 | 500 | 195 | 5.93 | 0.080 | 0.851 | 0.108 | 0.046 | 24.67 |
| | 650 | 600 | 230 | 3.03 | 0.046 | 0.483 | 0.080 | 0.025 | 28.36 |
| | 650 | 650 | 275 | 2.54 | 0.053 | 0.326 | 0.066 | 0.017 | 30.45 |
| | 750 | 650 | 360 | 28.95 | 1.289 | 5.821 | 0.194 | 0.380 | 13.79 |
| | 750 | 750 | 1310 | 34.63 | 1.390 | 7.388 | 0.188 | 0.443 | 12.49 |
| | 750 | 183 | 1475 | 28.59 | 1.139 | 6.477 | 0.203 | 0.447 | 14.50 |
| 8[h] | 750 | 188 | 70 | 34.15 | 0.718 | 8.338 | 0.196 | 0.533 | 13.77 |
| (Comparative) | 750 | 750 | 100 | 5.68 | 0.048 | 0.875 | 0.115 | 0.091 | 29.92 |
| | 750 | 800 | 190 | 9.85 | 0.083 | 1.523 | 0.134 | 0.188 | 28.27 |
| | 750 | 850 | 270 | 17.19 | 0.245 | 3.528 | 0.139 | 0.362 | 20.48 |
| | 750 | 864 | 310 | 21.82 | 0.350 | 4.499 | 0.134 | 0.406 | 18.06 |
| | 750 | 188 | 5975 | 10.46 | 0.082 | 1.596 | 0.161 | 0.170 | 27.55 |
| 9[i] A[j] | 750 | 185 | 85 | 21.08 | 1.063 | 1.188 | 0.365 | 0.665 | 46.49 |
| | 750 | 650 | 120 | 21.03 | 1.088 | 1.050 | 0.390 | 0.706 | 48.87 |
| | 750 | 700 | 185 | 20.02 | 1.027 | 0.878 | 0.417 | 0.698 | 52.22 |
| | 750 | 750 | 200 | 21.32 | 1.045 | 0.857 | 0.436 | 0.728 | 53.06 |
| | 750 | 750 | 1290 | 23.16 | 1.441 | 1.007 | 0.466 | 0.846 | 50.17 |
| B[k] | 750 | 750 | 1395 | 39.57 | 3.154 | 2.598 | 0.311 | 1.238 | 33.83 |
| (Comparative) | 750 | 188 | 1440 | 34.26 | 2.238 | 1.927 | 0.322 | 1.051 | 37.90 |
| | 750 | 188 | 1520 | 39.31 | 2.895 | 3.329 | 0.224 | 1.005 | 27.68 |
| | 750 | 750 | 1605 | 36.04 | 2.674 | 2.163 | 0.330 | 1.191 | 37.60 |
| | 750 | 850 | 1745 | 40.49 | 3.130 | 2.303 | 0.349 | 1.241 | 36.13 |
| | 750 | 185 | 1800 | 36.16 | 2.776 | 2.428 | 0.303 | 1.126 | 34.66 |
| | 750 | 185 | 2655 | 41.54 | 3.458 | 3.757 | 0.205 | 1.040 | 25.20 |
| C[l] | 750 | 185 | 2720 | 41.25 | 3.246 | 3.635 | 0.202 | 0.993 | 25.09 |
| (Comparative) | 750 | 185 | 2900 | 43.04 | 3.403 | 3.909 | 0.187 | 0.960 | 23.39 |
| D[m] | 750 | 185 | 3055 | 41.54 | 3.444 | 4.064 | 0.185 | 0.946 | 22.48 |
| (Comparative) | 750 | 750 | 3115 | 39.36 | 3.217 | 2.783 | 0.264 | 1.079 | 30.23 |

TABLE III-continued

| Example Sel. % | Reactor Temp. °C. | CH₄ Preheat Temp. °C. | Time (min) | CH₄ Conv. % | Product Gas Composition | | | | Total C₂ Sel. % |
|---|---|---|---|---|---|---|---|---|---|
| | | | | | % CO₂ | % CO | % C₂H₆ | % C₂H₄ | |
| | 750 | 750 | 4590 | 28.31 | 2.127 | 1.784 | 0.344 | 0.752 | 35.18 |

Footnotes:

<sup>a</sup>In this comarative example, no catalyst and no volatile component are used.

<sup>b</sup>In the comparative example, the effect of volatilized component is shown. In the cup in the upper part of the reactor, 5 grams of hydrated cesium hydroxide (from Johnson Matthey/Aesar Group, Seabrook, NH, Lot number 1403, 99.9 weight percent salt with 15-20% water) are used. The cesium hydroxide particle size is 100+ mesh (U.S. Sieve Series). At the completion of the experiment, cesium hydroxide (about 3.9 grams) covers the walls of the reactor.
The experiment demonstrates the reduction in vapor phase alkane conversion due to the presence of a volatilized compound of cesium hydroxide.

<sup>c</sup>In this comparative example, 1.4 grams of lithium hydroxide (from Johnson Matthey/Aesar Group, Seabrook, NH, Lot number GO9E, 99.3 weight percent) is placed in the cup. The catalyst particle size is 100+ mesh (U.S. Sieve Series). Most of the lithium hydroxide is volatilized out of the cup during the reaction.

<sup>d</sup>In this comparative example, 5 grams of cesium chloride (from Johnson Matthey/Aesar Group, Seabrook, NH, Lot number S94942, 99.999 weight percent, particle size is 100+ mesh, U.S. Sieve Series) are placed in the cup, and are observed after the experiment to have melted. The effect of the volatilized component is readily observed when the temperature of the upper oven is decreased to 226° C. when little cesium chloride is volatilized.

<sup>e</sup>In this comparative example, 2 grams of lithium chloride (from Johnson Matthey/Aesar Group, Seabrook, NH, Lot number S94408, 99.999 weight percent) are placed in the cup. The catalyst particle size is 100+ mesh (U.S. Sieve Series). After the reaction, the cup contains less than 1.73 grams of lithium compound. This example shows that the vapor phase alkane conversion reactions are altered by the addition of the volatile lithium component.

<sup>f</sup>Cesium chloride (5 grams, particle size 100+ mesh, U.S. Sieve Series, from Johnson Matthey/Aesar Group, Seabrook, NH, Lot number S94942, 99.999 weight percent) are placed in the cup and 38.23 grams of alpha aluminum oxide (14 to 30 mesh, U.S. Sieve Series, from Norton Company, Akron, OH, Sample number 8883119, Type SA 5451, B.E.T. surface area 0.27 square meter per gram, measured with a nitrogen flow method) are placed in the reaction zone.
About 4.9 grams of cesium compound are present in the reactor cup after the reaction.

<sup>g</sup>In the comparative example, 4 grams of ruthenium dioxide (100+ mesh, U.S. Sieve Series, from Alfa Products, Danvers, MA, Lot number B24H, 99.9 weight percent) are placed in the cup. After the reaction, 3.95 grams of ruthenium compound are present in the cup.

<sup>h</sup>In the comparative example, 5 grams of cesium chloride (100+ mesh, U.S. Sieve Series, from Johnson Matthey/Aesar Group, Seabrook, NH, Lot number S94942, 99.999 weight percent) are placed in the cup. About 4.9 grams of material remains in the cup at the end of the run.

<sup>i</sup>Cesium chloride (5 grams, 100+ mesh, U.S. Sieve Series, from Johnson Matthey/Aesar Group, Seabrook, NH, Lot number S94942, 99.999 weight percent) is placed in the cup, and 4 grams of a used catalyst, 30 to 60 mesh (U.S. Sieve Series), consisting of 9.1 weight percent barium carbonate (4.5 weight percent barium) on alpha aluminum oxide (from Norton Company, Akron, OH Sample number 8883119, Type SA 5451, B.E.T surface area 0.27 square meter per gram) are placed in
the reaction zone. The barium catalyst is made by stirring a mixture of 40 milliliters of water, 10 grams of alpha alumina, and 1.0 gram of barium carbonate (from Johnson Matthey/Aesar Group, Seabrook, NH, Lot number S97090R, 99.997 weight percent) until most of the water is evaporated. The material is then dried further in a 130° C. oven under a vacuum of 16–84 kPa for 20 hours, then is is calcined at 850° C. for 4 hours at atmospheric pressure in air.
Five grams of this catalyst is reacted with 80 volume percent methane, 10 volume percent oxygen, 10 volume percent nitrogen, and from 5 to 20 ppmv ethyl chloride for 151 hours at 750° C. At the end of this time, the methane conversion is 7 percent and the C₂ selectivity is 70 percent, prior to use in the example.

<sup>j</sup>Approximately 20 ppmv (parts per million by volume) of ethyl chloride are added to the methane inlet stream of the reactor.

<sup>k</sup>The total flow rate is 80 sccm and the ethyl chloride level is 40 ppmv.

<sup>l</sup>The total flow rate to the reactor is 80 sccm and the ethyl chloride level is 10 ppmv.

<sup>m</sup>The total flow rate to the reactor is 80 sccm and the ethyl chloride level is 20 ppmv.

It is claimed:

1. A process for oxidative coupling of alkane of 1 to 3 carbon atoms to heavier hydrocarbon comprising contacting the alkane in the presence of reactive oxygen-containing material under oxidative coupling conditions with a catalytically-effective amount of oxidative coupling catalyst contained in a reaction zone and feeding to the reaction zone intermittently or continuously an amount of at least one volatilized metal compound comprising metal which is more basic than lithium other than volatilized aluminum sufficient to inhibit the rate of vapor phase alkane conversion reactions.

2. The process of claim 1 wherein the volatilized metal compound comprises at least one of the group consisting of alkali metal compound and alkaline earth metal compound.

3. The process of claim 1 wherein the volatilized metal compound has a boiling point temperature under the reaction conditions of temperature and pressure which is higher than the reaction temperature.

4. The process of claim 2 wherein the volatilized metal compound comprises alkali metal hydroxide or salt.

5. The process of claim 4 wherein the alkali metal comprises cesium.

6. The process of claim 5 wherein the volatilized metal compound comprises cesium chloride.

7. The process of claim 4 herein the volatilized metal compound comprises halide salt.

8. The process of claim 7 wherein the halide salt is one or more of chloride, bromide and iodide.

9. The process of claim 1 wherein the reactive oxygen-containing material comprises oxygen.

10. The process of claim 1 wherein a halogen-containing vapor phase additive is provided to the reaction zone during the process.

11. The process of claim 10 wherein the catalyst comprises at least one of the group consisting of barium compound and strontium compound.

12. The process of claim 11 wherein the least one barium and/or strontium compound comprises at least one of oxide, peroxide, hydroxide, carbonate, chloride, bromide and iodide.

13. The process of claim 11 wherein barium and/or strontium compound comprises 0.1 to 20 weight percent of the catalyst.

14. The process of claim 11 wherein the halogen-containing vapor phase additive comprises at least one of hydrogen halide, organic halide of 1 to 3 carbon atoms and halogen, wherein the halide or halogen is at least one of chlorine, bromine and iodine.

15. The process of claim 14 wherein the halogen-containing vapor phase additive is provided in an amount of about 1 to 1000 ppm based on the fed to the reaction zone.

16. The process of claim 14 wherein the oxidative coupling conditions comprise a temperature between about 600° C. and 800° C.

17. The process of claim 8 wherein the mole ratio of alkane to oxygen atom is about 1:1 to 20:1.

* * * * *

UNITED STATES PATENT AND TRADEMARK OFFICE
CERTIFICATE OF CORRECTION

PATENT NO. : 5,073,657
DATED : December 17, 1991
INVENTOR(S) : Barbara K. Warren It is certified that error appears in the above-identified patent and that said Letters Patent is hereby corrected as shown below:

Column 1, line 64, before the word "higher" insert --selectivity to--.

Column 7, line 64, "(Ba(XO$_2$)" should read --(Ba(XO$_2$)$_2$)--.

Signed and Sealed this

Fifteenth Day of June, 1993

Attest:

MICHAEL K. KIRK

Attesting Officer

Acting Commissioner of Patents and Trademarks